(12) United States Patent
Walter et al.

(10) Patent No.: US 10,646,715 B2
(45) Date of Patent: May 12, 2020

(54) PARASYMPATHETIC ACTIVATION BY VAGUS NERVE STIMULATION

(71) Applicant: UNITED STATES GOVERNMENT AS REPRESENTED BY THE DEPARTMENT OF VETERANS AFFAIRS, Washington, DC (US)

(72) Inventors: James Walter, Oak Park, IL (US); Donald Thomas, Salinas, CA (US); Scott Sayers, Hinsdale, IL (US); Sanjay Singh, Oakbrook Terrace, IL (US); Raymond Dieter, Glen Ellyn, IL (US)

(73) Assignee: UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 348 days.

(21) Appl. No.: 15/328,386

(22) PCT Filed: Jul. 23, 2015

(86) PCT No.: PCT/US2015/041839
§ 371 (c)(1),
(2) Date: Jan. 23, 2017

(87) PCT Pub. No.: WO2016/014857
PCT Pub. Date: Jan. 28, 2016

(65) Prior Publication Data
US 2017/0209700 A1    Jul. 27, 2017

Related U.S. Application Data

(60) Provisional application No. 62/028,108, filed on Jul. 23, 2014.

(51) Int. Cl.
*A61N 1/36* (2006.01)
*A61N 1/05* (2006.01)
*A61N 1/372* (2006.01)

(52) U.S. Cl.
CPC ........ *A61N 1/36114* (2013.01); *A61N 1/0551* (2013.01); *A61N 1/0558* (2013.01);
(Continued)

(58) Field of Classification Search
CPC ............ A61N 1/36114; A61N 1/36175; A61N 1/36171; A61N 1/0558; A61N 1/0551;
(Continued)

(56) References Cited

U.S. PATENT DOCUMENTS

| 6,934,583 B2 | 8/2005 | Weinberg et al. |
| 8,401,640 B2 | 3/2013 | Zhao et al. |

(Continued)

FOREIGN PATENT DOCUMENTS

| WO | 9510227 A1 | 4/1995 |
| WO | 2016014857 A1 | 1/2016 |

OTHER PUBLICATIONS

International Search Report and Written Opinion dated Oct. 15, 2015 for related International Application No. PCT/US2015/041839, in 10 pages.

(Continued)

*Primary Examiner* — Mark Bockelman
(74) *Attorney, Agent, or Firm* — Ballard Spahr LLP

(57) ABSTRACT

The vagus nerve and branches of the vagus nerve are stimulated below the laryngeal nerve branch bifurcation in order to induce desired parasympathetic responses, such as decreased heart rate, without also triggering any adverse sympathetic responses. Stimulating surfaces of an open field bipolar electrode are positioned on or inserted through the pleural membrane overlying the vagus nerve at a location (Continued)

having substantially no cardiac sympathetic fibers adjacent to the vagus nerve. The open field bipolar electrodes can be securable-wire, needle, plate, or any other type of electrode suitable for being secured to the pleural membrane using one or more fastening mechanisms. Electrical stimuli are generated by a stimulator connected to the stimulating surfaces of the open field bipolar electrode by one or more leads.

11 Claims, 3 Drawing Sheets

(52) U.S. Cl.
CPC ..... *A61N 1/36053* (2013.01); *A61N 1/36171* (2013.01); *A61N 1/36175* (2013.01); *A61N 1/37235* (2013.01); *A61N 1/37247* (2013.01)

(58) Field of Classification Search
CPC ............ A61N 1/37235; A61N 1/36053; A61N 1/37247
See application file for complete search history.

(56) References Cited

U.S. PATENT DOCUMENTS

| | | |
|---|---|---|
| 8,406,868 B2 | 3/2013 | Buschman et al. |
| 8,509,919 B2 | 8/2013 | Yoo et al. |
| 8,577,458 B1 | 11/2013 | Libbus et al. |
| 8,620,450 B2 | 12/2013 | Tockman et al. |
| 8,626,299 B2 | 1/2014 | Gross et al. |
| 2004/0172089 A1 | 9/2004 | Whitehurst et al. |
| 2007/0027482 A1 | 2/2007 | Parnis et al. |
| 2007/0027483 A1 | 2/2007 | Maschino et al. |
| 2011/0301658 A1 | 12/2011 | Yoo et al. |

OTHER PUBLICATIONS

Schwartz, P.J., et al. "Sympathetic-parasympathetic interaction in health and disease: abnormalities and relevance in heart failure," Heart Fail Rev 2011;16:101-107.
Singh, S., et al. "Hypertrophy of neurons within cardiac ganglia in human, canine, and rat heart failure: the potential role of nerve growth factor," J Am Heart Assoc 2013;2:e000210, 1-12.
Bibevski, S., et al. "Evidence for impaired vagus nerve activity in heart failure," Heart Fail Rev 2011;16:129-135.
Sun, J., et al. "Unilateral vagus nerve stimulation improves ventricular autonomic nerve distribution and functional imbalance in a canine heart failure model," Int J Clin Exp Med 2015;8(6):9334-9340.
Zhang, Y., et al. "Arrhythmias and vagus nerve stimulation," Heart Fail Rev 2011;16:147-61.
Camm, A.J., et al. "Vagal nerve stimulation in heart failure," Eur Heart J 2015;36:404-406.
Tracey, K.J., "Physiology and immunology of the cholinergic antiinflammatory pathway," J Clin Invest 2007;117:289-296.
Bibevski, S., et al. "Ganglionic mechanisms contribute to diminished vagal control in heart failure," Circulation 1999;99:2958-2963.
Tu, H., et al. "Heart failure-induced changes of voltage-gated Ca2+ channels and cell excitability in rat cardiac postganglionic neurons," Am J Physiol Cell Physiol 2014;306:C132-C142.
Zannad, F., et al. "Chronic vagal stimulation for the treatment of low ejection fraction heart failure: results of the neural cardiac therapy for heart failure (NECTAR-HF) randomized controlled trial," European Heart Journal, 2015;36:425-433.
De Ferrari GM, et al. "Vagus nerve stimulation: from pre-clinical to clinical application: challenges and future directions," Heart Fail Rev 2011;16:195-203.
Sayers, S.T., et al. "Stimulation along the vagal pre and postganglionic pathway to selectively enhance vagal tone to the heart," The Open Cardiovascular and Thoracic Surgery Journal 2013; 6:7-15.
Tosato, M., et al. "Closed-loop control of the heart rate by electrical stimulation of the vagus nerve," Med Biol Eng Comput 2006;44:161-169.
Bishop, V.S., et al. "Role of vagal afferents in cardiovascular control," Vagal Control of the Heart: Experimental Basis and Clinical Implications 1994:325-344.

PARASYMPATHETIC ACTIVATION BY VAGUS NERVE STIMULATION

BACKGROUND

Field of the Invention

The present invention is generally related to treatment of heart failure and is more specifically related to vagus nerve stimulation to induce parasympathetic activation.

Related Art

Congestive heart failure (CHF) is characterized by a sustained decrease in the heart's pumping ability usually due to ventricular contractile dysfunction. CHF results in decreased blood delivery to the body and an accumulation of blood on the venous side of the circulatory system. One consequence of CHF is long term deleterious effects on cardiac function caused by an activation of both the sympathoadrenal and the renin-angiotensin-aldosterone system. CHF also causes drops in vagal and parasympathetic activities, leading to a decrease in the release of acetylcholine and activation of cardiac muscarinic receptors. On the one hand, the activation of cardiac muscarinic receptors generally suppresses atrial pacemaker activity, slows the rate of excitation spreading from the atrium to the ventricles, and decreases the contractility and conduction rate of both the atrium and the ventricle. Meanwhile, the benefits of vagal activity are largely diminished, such as its antagonistic effects on the release of catecholamines from sympathetic nerve terminals and anti-inflammatory immune responses.

The vagus nerve is part of the automatic nervous system that controls involuntary bodily functions, including heart rate. Patients experiencing CHF exhibit a lack of parasympathetic input to the heart. Thus, vagal nerve stimulation has proven to be an effective treatment for heart failure. In one recent clinical study conducted by Schwartz, the right vagus nerve was stimulated using a cuff electrode. The treatment included application of electric pulse stimulation at an average frequency of 2 to 4 Hertz and with currents ranging from 4 to 5 mA to achieve a reduction in heart rate. The electric pulses were delivered during the refractory period of the ventricles using higher frequency pulse trains. On the one hand, the Schwartz study reported a number of positive outcomes, including improvements in patient symptoms based on New York Heart Association's (NYHA) functional classification system. Treated patients, for instance, were able to sustain greater levels and extent of physical activities, such as longer periods of walking. Results of the study additionally demonstrated improved left ventricular end-systolic volume and end-diastolic volume in patients 3, 6, and 12 months post-implant. However, the study also revealed a number of negative side effects, particularly ones associated with the selection of treatment site.

In the Schwartz study, vagal nerve stimulation was performed in the neck region of the participating patients, which is consistent with the prevailing practice. In human beings, vagal nerve stimulation is typically performed by applying electrical stimulation to the portion of the vagus nerve that traverses the neck region. The neck region is a common stimulation site because the human vagus nerve tends to be more accessible for electrical stimulation by conventional electrodes in that particular region. Vagal nerve stimulation in the neck obviates risky surgical procedures and can be performed under local anesthesia. However, vagal nerve stimulation in the neck can also cause a litany of negative side effects. As was reported in the Schwartz study, stimulating the vagus nerve in the neck region can cause transient hoarseness, coughing, and pronounced sensation of electrical stimulation and discomfort. Consequently, for patients treated according to the Schwartz methodology, the duration of each continuous stimulation period is limited.

SUMMARY

To reduce or to avoid the side effects of conventional treatment methods, the apparatus and method described herein are directed toward stimulation of the vagus nerve at a select location other than the neck region. Applications of the apparatus and methods described herein are highly beneficial for patients with chronic heart failure and are also beneficial during open heart surgery, a period when vagal parasympathetic effects on the heart are reduced. In some embodiments, cardiac branches of the vagus nerve are stimulated below the laryngeal nerve bifurcation, an area of the vagus nerve located in the right upper chest below the branching point of the recurrent laryngeal nerve. In some embodiments, stimulation is applied to the vagus nerve and caudal cardiac branch of the vagus nerve below the laryngeal nerve branch bifurcation from the vagus nerve. Advantageously, stimulating the vagus nerve and branches of the vagus nerve below the laryngeal nerve branch bifurcation has been shown to slow the heart rate with minimal side effects. For example, stimulating the branches of the vagus nerve below the laryngeal nerve bifurcation results in parasympathetic activation without disturbing nearby sympathetic nerve fibers and triggering any adverse sympathetic responses (e.g., increased heart rate). In addition, some embodiments of the apparatus and method described herein are directed toward a minimally invasive means of implanting an electrode in the upper thorax. For example, vagal stimulation is performed without the placement of a cuff around the nerve (i.e., cuff electrode).

Instead, in some embodiments, an open field electrode is placed on the pleural membrane overlying the vagus nerve or through the pleural membrane overlying the vagus nerve. In humans, there is minimal musculature where the vagus nerve is located in the upper thorax and the vagus nerve and its branches are isolated from sensory nerves by the tracheal and lungs allowing for vagal stimulation without discomfort. Thus, in embodiments where the vagus nerve is stimulated in the upper thorax, open field electrodes are superior since open field electrodes entail a less complicated and less invasive implantation procedure than cuff electrodes. However, use of an open field electrode can stimulate nearby sympathetic nerve fibers and trigger adverse sympathetic responses (e.g., increased heart rate). Some embodiments of the apparatus and method described herein are directed toward the use of a needle type electrode. In some embodiments, vagal stimulation in the upper thorax is performed using a securable-wire electrode. The securable-wire electrode is akin to the needle electrodes used in earlier studies but offers more clinical utility as it can be placed closer to the vagus nerve. This is a particularly useful feature in cases where there is copious fat surrounding the nerve or where the branches of the vagus nerve are distant from the pleural membrane. In addition, a securable-wire electrode can be attached more easily to the pleural membrane.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments disclosed herein provide for an apparatus and a method of stimulating the vagus nerve in the upper thorax in order to cause parasympathetic activation in patients suffering from heart failure. For example, the vagus nerve trunk or alternatively branches of the vagus nerve are stimulated below the laryngeal nerve bifurcation using open field electrodes (e.g., small plate electrode, epimysial electrode, fascial electrode, needle electrode, securable-wire electrode, etc.). After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

INTRODUCTION

Use of isolated field electrodes (e.g., cuff electrode) for vagal stimulation in the neck area has many drawbacks. The inventors have recognized that vagal stimulation below the laryngeal nerve bifurcation provides substantial improvement of many of these drawbacks. However, implantation of an isolated field electrode below the laryngeal nerve bifurcation is undesirable. Accordingly, the inventors have recognized that use of an open field electrode (e.g., small plate electrode, epimysial electrode, fascial electrode, needle electrode, securable-wire electrode, etc.) is superior for implantation because open field electrodes entail a less complicated and less invasive implantation procedure. However, use of an open field electrode below the laryngeal nerve bifurcation may cause undesirable stimulation of nearby cardiac sympathetic nerve fibers that come from the sympathetic chain ganglia (e.g., from the cervical and stellate sympathetic ganglia) and thereby trigger adverse sympathetic responses such as increased heart rate. The inventors have therefore also recognized that the specific implantation location of the open field electrode (specifically, the simulating surfaces of the open field electrode) is paramount for realizing the significant benefits of parasympathetic activation while minimizing the significant drawbacks of adverse sympathetic responses triggered by stimulation of nearby cardiac sympathetic nerve fibers. While the specific location may vary from patient to patient, the optimal implantation location is generally between 1 cm and 10 cm below (caudal or distal to) the laryngeal nerve bifurcation from the vagus nerve.

Figure 1:
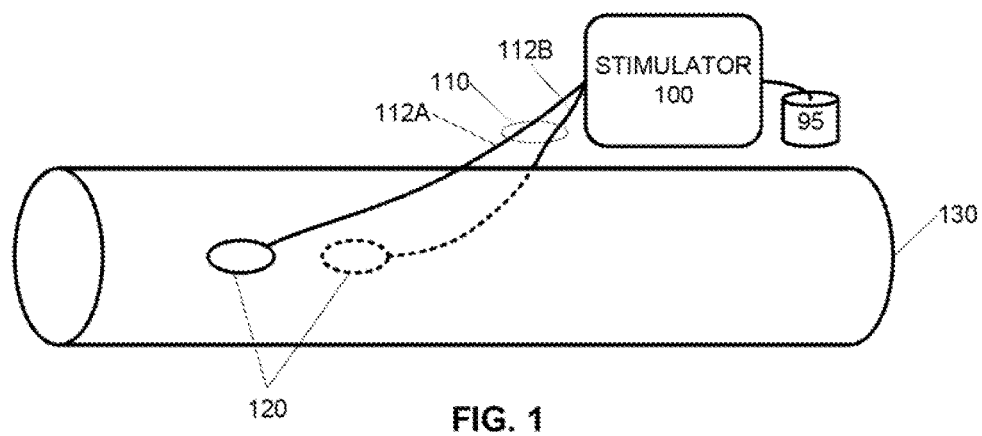
FIG. 1 is a diagram illustrating an example apparatus for stimulating the vagus nerve according to an embodiment.

FIG. 1 is a diagram illustrating an example apparatus for stimulating the vagus nerve 130 according to an embodiment. In some embodiments, the apparatus is used to stimulate the vagus nerve 130 in the upper thorax. For example, the apparatus can be used to stimulate the vagus nerve 130 below the laryngeal nerve bifurcation. The portion of the vagus nerve 130 that is stimulated may be the main vagus nerve trunk or may be one or more branches of the vagus nerve 130.

As shown in FIG. 1, apparatus includes a stimulator 100 and a bipolar stimulating electrode 110, which may comprise one or more leads 112A, 112B each having one or more stimulating surfaces 120 arranged in a bipolar configuration. In some embodiments, the leads 112A, 112B are coated with an insulating material, such as Teflon® or any other appropriate material. The stimulating surface 120 on each electrode may comprise an uncoated or uninsulated portion of the electrode. In alternative embodiments, the stimulating surface 120 may have a variety of shapes such as a rectangle, an arrow/point, an oval, a circle, or the like. Advantageously, the shape of the stimulating surface 120 may be selectively optimized for the location in which the stimulating surface 120 is deployed (e.g., on an outer surface of the pleural membrane or between the vagus nerve and an inner surface of the pleural membrane). Each of the two leads 112A, 112B comprising the bipolar stimulating electrode is attached at a proximal end to the stimulator 100 and in electrical communication with the stimulator 100. In an embodiment, the stimulator 100 is located inside the body. In an alternative embodiment, the stimulator 100 is located outside of the body.

The stimulator 100 comprises a power source for generating electrical stimuli and a memory 95 for storing operating parameters and instructions and the like. The stimulator may include communication interfaces for receiving instructions from a separate device via a wired or wireless communication link. The power source may be internal (e.g., battery) or external (e.g., power supply connected to an external power source such as an electrical grid). The stimulator 100 comprises a processor configured to control the operation of the stimulator 100 in accordance with predetermined instructions or instructions received dynamically in real time. An example hardware embodiment of stimulator 100 is later described with respect to FIG. 5.

FIG. 1 illustrates that the stimulating surfaces 120 in the bipolar configuration are placed within close proximity of the vagus nerve 130. In some embodiments, the electrode 110 comprises an open field electrode. As such, in some embodiments, the stimulating surfaces 120 can be positioned without an isolating cuff. According to the embodiments describe herein, the stimulating surfaces 120 can be placed adjacent to the vagus nerve 130 by attaching or securing the electrodes to an outer surface of the pleural membrane in a number of different ways. For example, the leads 112A, 112B can be secured using sutures, self-securing barbs, surgical glue, mesh, corkscrew wire, or any other appropriate fastening mechanisms. Securing means that attach the electrode 110 to physical structures on or near the vagus nerve 130 can be applied at one or more locations along the leads 112A, 112B and stimulating surfaces 120 of the electrode 110.

In some embodiments, apparatus 100 is used to stimulate branches of the vagus nerve 130 in the upper-thorax as therapy for patients suffering from heart failure. In some embodiments, stimulating parameters, including frequencies that range from 4 Hertz to 20 Hertz, are used in order to induce the desired vagal effects, such as a decrease in heart rate. Stimulating the vagus nerve 130 with an excessively large current is known to cause negative side effects (e.g., paraspinal muscle stimulation). Additionally, high stimulating currents may induce supraventricular arrhythmia. In some embodiments, the main vagus nerve trunk or branches of the vagus nerve 130 are stimulated according to stimulating parameters that include current amperage ranging from 1 mA to 12 mA. In some embodiments, a stimulating pulse duration of 300 μs is optimal for stimulating the small parasympathetic fibers in the vagus nerve or its branches that innervate the heart. In some embodiments, the stimulating pulse duration can range from 200 μs to 1000 μs. In some embodiments, duty cycles of stimulation are used in order to maintain effective stimulation. In one embodiment, the duty cycle can comprise a 10 second ON period and a 5 second OFF period. In some embodiments, the duty cycle can include a continuous ON period of up to 24 hours and a 1 to 2000 second OFF period for recovery.

In one embodiment, stimulation of the vagus nerve 130 is conducted to induce two to ten beats per minute of heart rate slowing. For example, initial stimulation may be conducted at a low frequency (e.g., 4 Hz) and a low current (e.g., 1 mA) for a low duration (e.g., 200 μs) and if the desired reduction in heart rate is not achieved, higher frequencies, current and duration may be employed singularly or in any combination until the desired heart rate reduction is achieved.

Figure 2A:
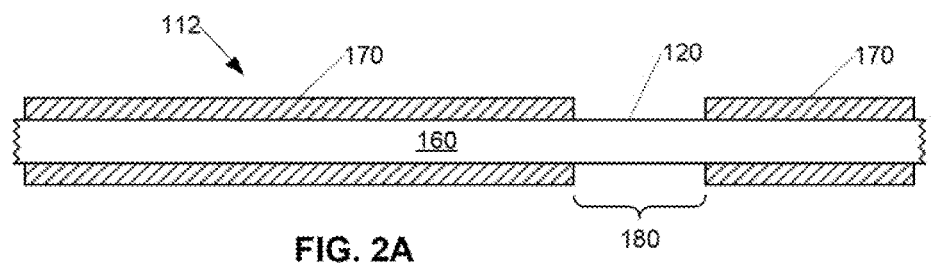
FIG. 2A is a diagram illustrating an example bipolar electrode lead according to an embodiment.

FIG. 2A is a diagram illustrating an example lead 112 of a bipolar electrode 110 according to an embodiment. In alternative embodiments, bipolar electrode 110 comprises an open field electrode, a wire electrode, a needle electrode, an epimysial electrode, a fascial electrode or any other type of electrode that can be configured to be positioned on or near the vagus nerve 130. Although only a single lead 112 is shown in FIG. 2A for the sake of simplicity, it will be understood that one or more leads 112 may be employed, with each lead 112 being electrically coupled to the stimulator 100.

According to the embodiment illustrated in FIG. 2A, the lead 112 comprises a conducting wire 160 that is at least partially surrounded by an insulating surface 170. The lead 112 additionally comprises one or more stimulating surfaces 120 in an exposed area 180 where the conducting wire 160 is not covered by the insulating surface 170. The exposed area 180, although shown in an interior portion of the lead 112, can alternatively be positioned at the distal end of the lead 112. In an embodiment having more than one stimulating surface 120 on an individual lead 112, the plural stimulating surfaces 120 may all be positioned in an interior portion of the lead 112 or one of the stimulating surfaces 120 may be positioned at the distal end of the lead 112 furthest away from the stimulator 100.

In some embodiments, portions of the leads 112 are insulated by the insulating surface 170 while other portions of the leads 112 are not insulated and create exposed areas 180. In some embodiments, the exposed areas 180 of the lead 112 comprise stimulating surfaces 120. For example, each of the leads 112 may contain at least one stimulating surface 120 in an exposed area 180. However, it may be desirable or necessary in some cases for each lead 112 to have multiple (i.e., two or more) stimulating surfaces 120. In some embodiments, the leads 112 and the stimulating surfaces 120 are positioned at a desired distance apart from one another. For example, the stimulating surface 120 on a first lead can be positioned 1 mm to 5 mm away from the stimulating surface 120 on a second lead.

Furthermore, in some embodiments, the stimulating surfaces 112 on the leads 112 are relatively small in size. For example, in order to achieve the desired parasympathetic effects, the vagus nerve and particularly those fibers that innervate the heart, must be stimulated with a concentrated electric current. In an embodiment where the electrode 110 comprises an open field electrode, the stimulating surfaces 120 are advantageously relatively small in size in order to produce high charge injection densities and thereby stimulate the vagus nerve 130 with the lowest possible current. For example, the stimulating surfaces 120 in such an embodiment can be between 0.5 mm to 5 mm long and 0.5 mm wide to 5 mm wide (e.g., an area of 0.25 $mm^2$ to 25 $mm^2$). In alternative embodiments, the area of the simulating surfaces 120 may be smaller, for example a length between 0.5 mm to 5 mm long and the width from 0.5 mm to 1.5 mm wide (e.g., an area of 0.25 $mm^2$ to 7.5 $mm^2$). In one embodiment, the stimulating surfaces 120 areas are cross-sectional areas and the actual area of exposed stimulating surface would be much greater if multi-stranded wire were used as the stimulating surface 120.

In alternative embodiments, the stimulating surfaces 120 are 0.5 mm to 1.5 mm in length and 0.5 mm to 1.5 mm in width. In other embodiments, the stimulating surfaces 120 are 1 mm to 2 mm in length and 1 mm to 2 mm in width. Advantageously, a small area of the stimulating surface 120 generates a contained electric field and avoids the negative consequences associated with spreading the electric field.

According to the embodiments described herein, conducting wire 160 can be made of any appropriate conductive material that is both corrosion and fracture resistant (e.g., platinum). In other words, the stimulating surfaces 120 at the exposed areas 180 of the leads 112 can be made of any conductive material that is resistant to corrosion and fracture, such as platinum, 316 LVM stainless steel, or any suitable equivalent. In some embodiments, the insulating surface 170 surrounding the conducting wire 160 may comprise a single enclosure such as a tube. In some embodiments, post insertion, leads 112 are secured to the pleural membrane 200 surrounding the vagus nerve 130. In some embodiments, leads 112 are secured to the pleural membrane 200 at its entry point and exit point through the pleural membrane 200. In some embodiments, the leads 112 can be secured to the pleural membrane 200 using any appropriate fastening mechanisms, including but not limited to surgical clips, sutures, barbs, corkscrew wire, mesh, curved surfaces (e.g., coils) and the like. In some embodiments, the insertion needle 190 that is initially attached to the leads 112 is removed (e.g., cut off) once the leads 112 are secured at an appropriate position, such as the entry and exit point through the pleural membrane 200.

Figure 2B:
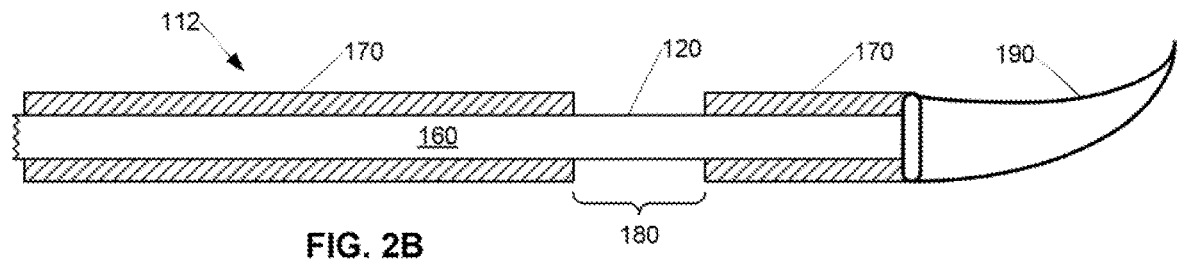
FIG. 2B is a diagram illustrating an example bipolar electrode lead having an insertion needle according to an embodiment.

FIG. 2B is a diagram illustrating an example bipolar electrode lead 112 having an insertion needle 190 according to an embodiment. Although only a single lead 112 is shown in FIG. 2B for the sake of simplicity, it will be understood that one or more leads 112 may be employed, with each lead 112 being electrically coupled to the stimulator 100 at the proximal end and connected to the insertion needle 190 at the distal end. In some embodiments, the insertion needle 190 is used to position the lead 112 and its corresponding stimulating surfaces 120 in proximity of the vagus nerve 130 and the insertion needle 190 is also configured to be removed once the lead 112 and its corresponding stimulating surfaces 120 is implanted. For example, in one embodiment, the insertion needle 190 is used for the initial placement of the one or more leads 112 and then the insertion needle 190 is removed (e.g., cut off) after the leads 112 are secured.

In one embodiment, the insertion needle 190 is configured to guide the lead 112 and its corresponding stimulating surfaces 120 through the pleural membrane and around the vagus nerve. As will be discussed in more detail below, in alternative embodiments, the lead 112 and its corresponding stimulating surfaces 120 may be positioned and secured on or near an external surface of the pleural membrane 209. Thus, in certain embodiments, the lead 112 and its corresponding stimulating surfaces 120 can be positioned and secured without insertion needle 190.

Figure 2C:
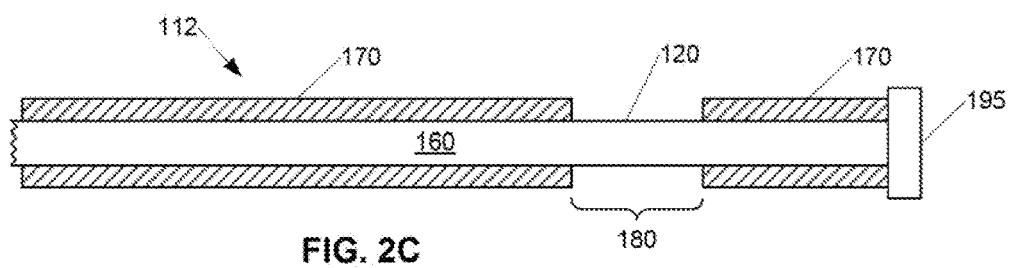
FIG. 2C is a diagram illustrating an example bipolar electrode lead having a cap according to an embodiment.

FIG. 2C is a diagram illustrating an example bipolar electrode lead 112 having a cap 195 according to an embodiment. Although only a single lead 112 is shown in FIG. 2C for the sake of simplicity, it will be understood that one or more leads 112 may be employed, with each lead 112 being electrically coupled to the stimulator 100. In some embodiments, such as the one shown in FIG. 2C, a cap 195 can be placed on the terminal or distal end of each lead 112. The cap 195 may be applied to the lead 112 prior to insertion of the lead 112 or alternatively may be applied to the lead 112 after the lead 112 has been positioned and secured. In one embodiment, the cap 195 is applied to the lead 112 after the lead 112 has been positioned and secured and the insertion needle 190 has been removed.

Figure 3A:
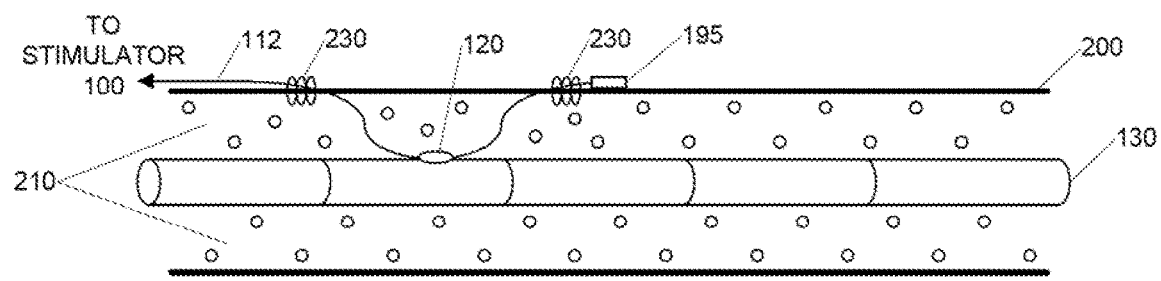
FIG. 3A is a diagram illustrating an example placement of stimulating surfaces near the vagus nerve according to an embodiment.

FIG. 3A is a diagram illustrating an example placement of stimulating surface 120 near the vagus nerve 130 according to an embodiment. Although only a single lead 112 is shown in FIG. 3A for the sake of simplicity, it will be understood that one or more leads 112 may be employed, with each lead 112 being electrically coupled to the stimulator 100 at its proximal end. In some embodiments described herein, electric stimuli are applied to the vagus nerve 130 between the vagus nerve 130 and the pleural membrane 200 that surrounds the vagus nerve. In FIG. 3A, the stimulating surface 120 is inserted through the pleural membrane 200 and traverses a layer 210 of fat and connective tissue surrounding the vagus nerve 130. In various embodiments, the stimulating surfaces 120 are placed in an appropriate position on or near the vagus nerve 130. As FIG. 3A illustrates, the stimulating surfaces 120 are positioned between the vagus nerve 130 and the pleural membrane 200. In one embodiment, the stimulating surfaces 120 are positioned closer to the vagus nerve 130 than the pleural membrane 200. In one embodiment, the stimulating surfaces 120 are placed as close to the vagus nerve 130 as possible. In an embodiment where the stimulating surfaces 120 are positioned between the vagus nerve 130 and an inner surface of the pleural membrane 200, the size of each stimulating surface 120 can be relatively smaller with a smaller overall surface area of the stimulating surface 120 because the electrical stimuli does not need to penetrate the tissue of the pleural membrane 200 in order to stimulate the vagus nerve 130.

FIG. 3A further shows that the leads 112 are secured to the pleural membrane 200 at one or both of the entry site and exit site. Different types of fastening means 230 can be used in the various embodiments described herein (e.g., suture, surgical clips, barbs, coils, mesh, corkscrew wire, and the like).

Figure 3B:
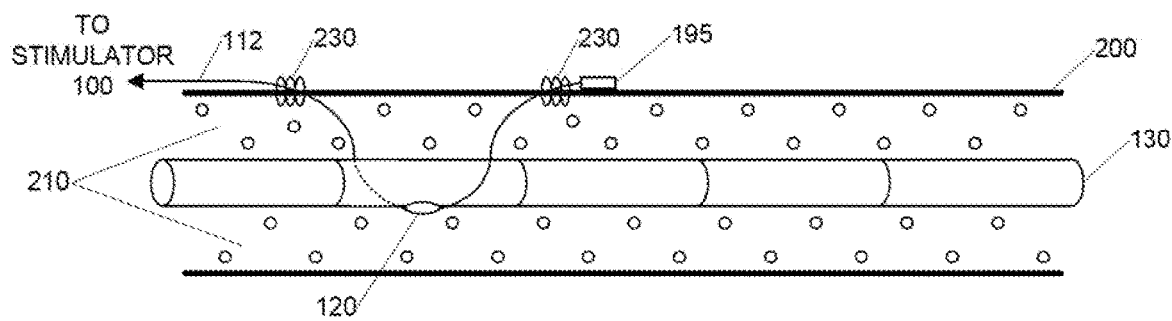
FIG. 3B is a diagram illustrating an example placement of stimulating surfaces near the vagus nerve according to an embodiment.

FIG. 3B is a diagram illustrating an example placement of stimulating surface 120 near the vagus nerve 130 according to an embodiment. Although only a single lead 112 is shown in FIG. 3B for the sake of simplicity, it will be understood that one or more leads 112 may be employed, with each lead 112 being electrically coupled to the stimulator 100 at its proximal end. As depicted in FIG. 3B, the vagus nerve 130 is surrounded by the pleural membrane 200. In some embodiments, branches of the vagus nerve 130 are stimulated beneath the pleural membrane 200. In one embodiment, the leads 112 and stimulating surfaces 120 of an electrode 110, such as a securable-wire electrode or bipolar electrode or epimysial electrode or fascial electrode, are inserted through the pleural membrane. FIG. 3B depicts the hammock position, wherein the leads 112 are placed under and around the vagus nerve 130. In various embodiments, the hammock position is used in order to better maintain the position of the stimulating surfaces 120 proximal to the vagus nerve 130. In some embodiments, an insertion needle, such as the one depicted in FIG. 2, is used to guide the leads 112 and their corresponding stimulating surfaces 120 into and out of the pleural membrane 200, and to help place the stimulating surfaces 120 in an appropriate position. For example, to achieve the placement desired for the hammock position, the insertion needle first enters the pleural membrane 200 at a first side of the vagus nerve 130, then travels beneath and around a second side vagus nerve 130 opposite the first side of the vagus nerve 130, and finally exits the pleural membrane 200 on substantially the same first side of the vagus nerve 130 where the insertion needle entered the pleural membrane 200. In some embodiments, the entry and exit points on the pleural membrane 200 for the leads 112 are an appropriate distance apart. For example, the leads 112 may enter and exit the pleural membrane 200 at least 2 cm apart. In some embodiments, the stimulating surfaces 120 are placed within close proximity of the vagus nerve 130. For example, in FIG. 3B, the stimulating surfaces 120 are placed according to the hammock position and are therefore positioned beneath the vagus nerve relative to the entry and exit points of the leads 112 through the pleural membrane 200. In other embodiments, the stimulating surfaces 120 are placed along the top or sides of the vagus nerve 130 relative to the entry and exit points of the leads 112 through the pleural membrane 200. In various embodiments, the stimulating surfaces 120 are placed as close to the vagus nerve 130 as possible. In an embodiment where the stimulating surfaces 120 are positioned between the vagus nerve 130 and an inner surface of the pleural membrane 200, the size of each stimulating surface 120 can be relatively smaller with a smaller overall surface area of the stimulating surface 120 because the electrical stimuli does not need to penetrate the tissue of the pleural membrane 200 in order to stimulate the vagus nerve 130.

Figure 3C:
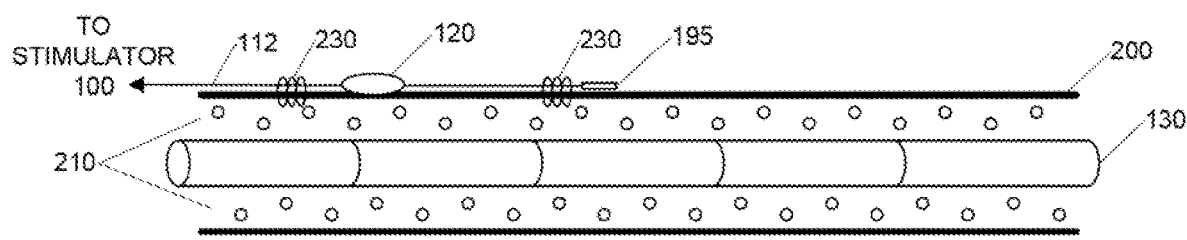
FIG. 3C is a diagram illustrating an example placement of stimulating surfaces near the vagus nerve according to an embodiment.

FIG. 3C is a diagram illustrating an example placement of stimulating surface 120 near the vagus nerve 130 according to an embodiment. Although only a single lead 112 is shown in FIG. 3C for the sake of simplicity, it will be understood that one or more leads 112 may be employed, with each lead 112 being electrically coupled to the stimulator 100 at its proximal end. As shown in FIG. 3C, the leads 112 and stimulating surfaces 120 may be positioned on and secured directly to an exterior surface of the pleural membrane 200. In certain areas of the human body, such as in the upper thorax, the pleural membrane 200 is situated within close proximity of the vagus nerve 130. For instance, the fat and tissue layer 210 between the pleural membrane 200 and the vagus nerve 130 can be minimal in this location. Thus, in certain embodiments, the stimulating surfaces 120 do not need to be inserted through the pleural membrane 200 in order to position the stimulating surfaces 120 close enough to the vagus nerve 130 to expose the vagus nerve 130 to adequate electric stimuli. FIG. 3C shows that the leads 112 and corresponding stimulating surfaces 120 are placed on and secured to the pleural membrane 200 without penetrating its surface. Additionally, the stimulating surfaces 112 remain outside the pleural membrane 200. In some embodiments, the vagus nerve 130 is stimulated through the pleural membrane 200 while the leads 112 and corresponding stimulating surfaces 120 are placed and secured without penetrating the pleural membrane 200. In some embodiments, avoiding the insertion of the leads 112 and corresponding stimulating surfaces 120 through the pleural membrane 200 expedites and simplifies the implantation process. In an embodiment where the stimulating surfaces 120 are positioned on or near the outside surface of the pleural membrane 200, the size of each stimulating surface 120 can be relatively larger with a larger overall surface area of the stimulating surface 120 because the electrical stimuli needs to penetrate the tissue of the pleural membrane 200 in order to stimulate the vagus nerve 130.

Figure 3D:
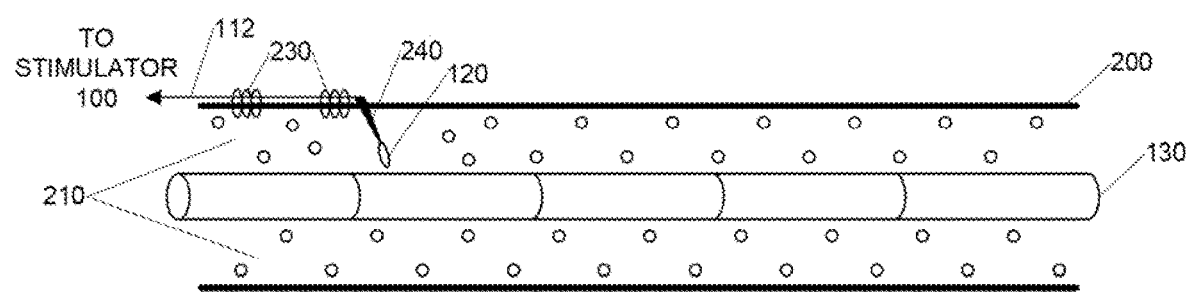
FIG. 3D is a diagram illustrating an example placement of stimulating surfaces near the vagus nerve according to an embodiment.

FIG. 3D is a diagram illustrating an example placement of stimulating surface 120 near the vagus nerve 130 according to an embodiment. Although only a single lead 112 is shown in FIG. 3D for the sake of simplicity, it will be understood that one or more leads 112 may be employed, with each lead 112 being electrically coupled to the stimulator 100 at its proximal end. Some of the embodiments described herein are directed towards the use of leads 112 where the stimulating surfaces 120 are located on the distal tips of the leads 112. In some embodiments, needle electrodes 110 having a pointed or small disk shape stimulating surface 120 are used to stimulate the vagus nerve 130. In some embodiments, the vagus nerve 130 is stimulated using needle electrodes 110 that are insulated except for regions or areas around the distal tip of the leads 112. As shown in FIG. 3D, the lead 112 comprises a tip 240 and a corresponding stimulating surface 120 that together comprise a needle-like structure. The needle-like structure is inserted through the pleural membrane 130 such that the stimulating surface 120 at the distal tip of the lead 112 is positioned near the vagus nerve 130.

In some embodiments, such as shown in FIGS. 3A, 3B, and 3D, the vagus nerve 130 is stimulated by applying electric stimuli between the vagus nerve 130 and the pleural membrane 200. In other embodiments, such as shown in FIG. 3C, the vagus nerve 130 is stimulated by applying electric stimuli through the pleural membrane 200. Although not shown in FIG. 3D, it is understood that in cases where the vagus nerve 130 is sufficiently close to the pleural membrane 200 (e.g., minimal intervening fat and connective tissue layer 210), the needle electrodes 110 may not fully penetrate the pleural membrane 200. Otherwise stated, in some embodiments, the vagus nerve is stimulated by needle electrodes 110 that are placed substantially on top of the pleural membrane 200 and secured to the pleural membrane 200 by fasteners 230. In an embodiment where the stimulating surfaces 120 are positioned between the vagus nerve 130 and an inner surface of the pleural membrane 200, the size of each stimulating surface 120 can be relatively smaller with a smaller overall surface area of the stimulating surface 120 because the electrical stimuli does not need to penetrate the tissue of the pleural membrane 200 in order to stimulate the vagus nerve 130. However, in an embodiment where the stimulating surfaces 120 are positioned on or near the outside surface of the pleural membrane 200, the size of each stimulating surface 120 can be relatively larger with a larger overall surface area of the stimulating surface 120 because the electrical stimuli needs to penetrate the tissue of the pleural membrane 200 in order to stimulate the vagus nerve 130.

In one embodiment, when the stimulating surface 120 is positioned between the vagus nerve 130 and the inner surface of the pleural membrane 200, a wire electrode or needle electrode is employed. In an alternative embodiment, when the stimulating surface 120 is positioned on or near the outer surface of the pleural membrane 200, a plate or fascial or epimysial electrode is employed.

In one embodiment, when the leads 112 and corresponding stimulating surfaces 120 are positioned adjacent to the vagus nerve 130, the stimulating surfaces 120 may be on the top or bottom or medial or lateral sides of the vagus nerve 130. In one embodiment, a lateral location relative to the vagus nerve 130 may be beneficial to reduce the risk of atrial arrhythmia due to stimulation.

Figure 4:
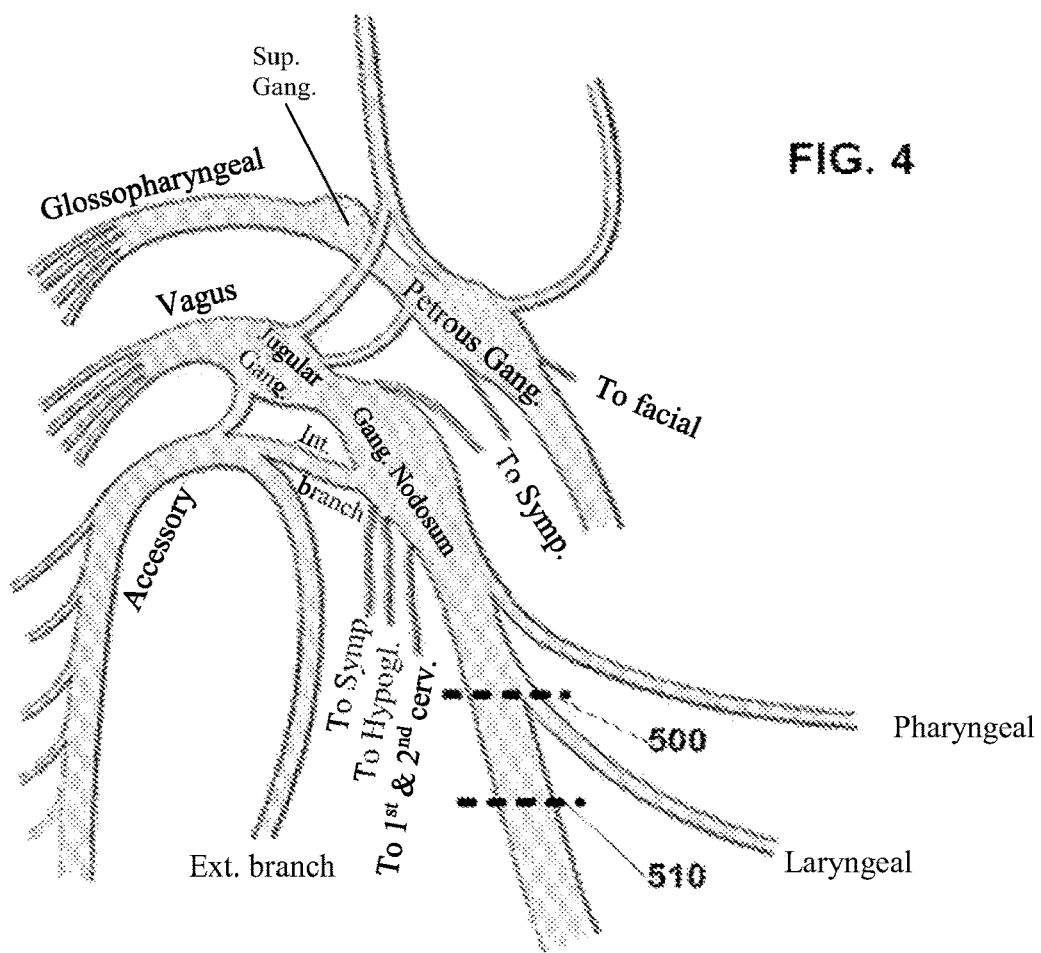
FIG. 4 is a diagram illustrating an example of the upper portion of the glossopharyngeal, vagus, and accessory nerves according to an embodiment.

FIG. 4 is a diagram illustrating an example upper portion of the glossopharyngeal, vagus, and accessory nerves according to an embodiment. As depicted in FIG. 4, several branches of the vagus nerve extend to the heart. However, sympathetic nerve fibers are found near the main trunk of the vagus nerve. Thus, some of the embodiments described herein are directed toward stimulation of the branches of the vagus nerve. In some embodiments, stimulator 100 is used to stimulate branches of the vagus nerve. In particular, in certain embodiments, stimulator 100 is used to stimulate the caudal cardiac branch of the vagus nerve. FIG. 4 further shows that stimulation of the vagus nerve in one embodiment takes place below the recurrent laryngeal nerve bifurcation 500. In particular, some of the embodiments described herein are directed towards stimulating the vagus nerve below the laryngeal nerve bifurcation 500 as heart failure therapy, since application of electric stimuli to that site is associated with minimal complications and side effects. In some embodiments, an apparatus (e.g., stimulator 100) is used to stimulate the vagus nerve below the laryngeal nerve bifurcation 500 in order to induce desired vagal effects, such as a decrease in heart rate. In some embodiments, electric stimuli are applied to the vagus nerve at any location 510 distal to the laryngeal nerve bifurcation 500. In some embodiments, a precise point on the vagus nerve 130 below the laryngeal nerve bifurcation 500 where electric stimuli are optimally applied is determined on an individual basis. For example, depending on the individual patient, the vagus nerve 130 can be optimally stimulated at a location that is between 1 cm and 10 cm below (caudal or distal to) the laryngeal nerve bifurcation 500.

Figure 5:
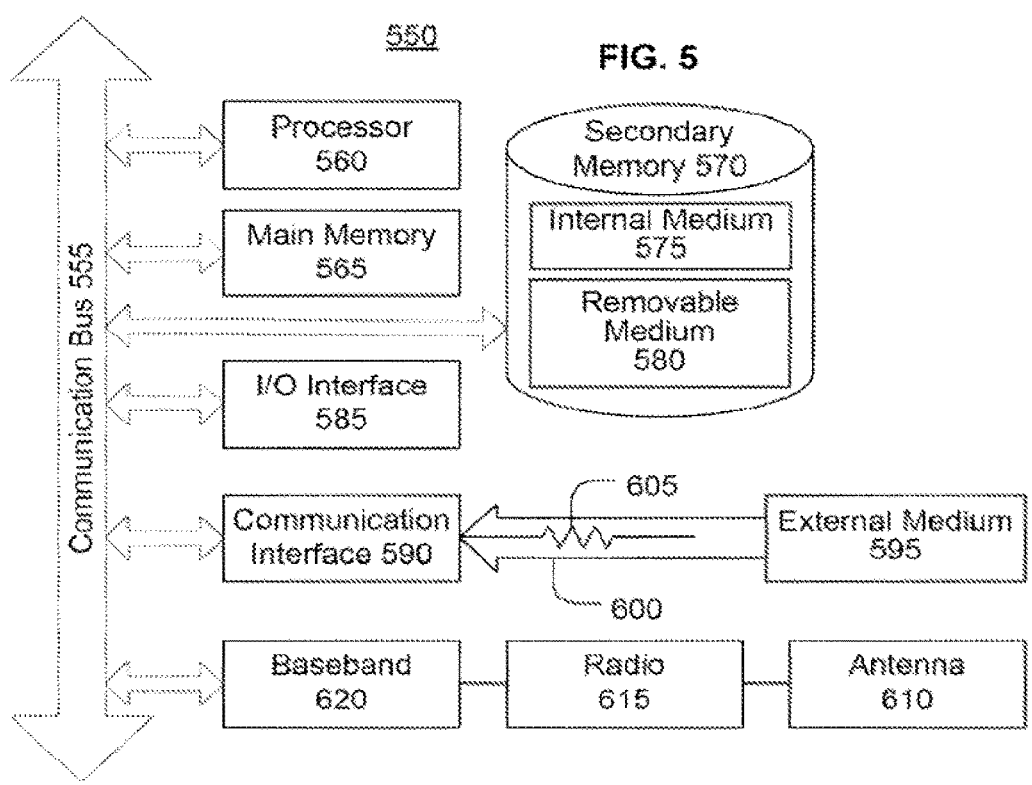
FIG. 5 is a block diagram illustrating an example wired or wireless processor enabled device that may be used in connection with various embodiments described herein.

FIG. 5 is a block diagram illustrating an example wired or wireless processor enabled device 550 that may be used in connection with various embodiments described herein. For example the system 550 may be used with the stimulator 100, as previously described with respect to FIG. 1. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

System 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display. The I/O interface 585 is capable of facilitating input from and output to various alternative types of human interface and machine interface devices alike. The I/O interface 585 may also be adapted to generate electrical stimuli and send the electrical stimuli to one or more electrodes (not shown) for delivery to stimulating surfaces (not shown). The I/O interface 585 may generate electrical stimuli from an internal or external power source such as a battery (now shown) or power supply (not shown) connected to an electrical grid.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few. The communication interface 590 advantageously can receive instructions regarding the parameters for electrical stimuli to be generated by the I/O interface 585. Such parameters may include but are not limited to the stimulating frequency, current amperage and duration, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A method comprising:
   securing one or more stimulating surfaces near a portion of a vagus nerve between 1 cm and 10 cm below a laryngeal nerve bifurcation, wherein said portion of the vagus nerve has substantially no adjacent cardiac sympathetic fibers;
   delivering electric stimuli to the one or more stimulating surfaces based at least in part on one or more stimulating parameters; and
   stimulating said portion of the vagus nerve by creating an electrical field in response to said electric stimuli, wherein the one or more stimulating surfaces are positioned outside of a pleural membrane at least partially surrounding the vagus nerve.

2. The method of claim 1, wherein the portion of the vagus nerve is a main trunk portion of the vagus nerve.

3. The method of claim 1, wherein the portion of the vagus nerve is one of a plurality of cardiac branches of the vagus nerve.

4. The method of claim 1, wherein the one or more surfaces are secured to the pleural membrane using one or more of the following: sutures, surgical clips, surgical glue, barbs, coils and mesh.

5. The method of claim 1, wherein the one or more stimulating parameters include an electric pulse frequency selected from a range of 3 Hertz to 20 Hertz.

6. The method of claim 1, wherein the one or more stimulating parameters include an electric pulse duration selected from a range of 200 μs to 1000 μs.

7. The method of claim 1, wherein the one or more stimulating parameters include an electric current amperage selected from a range of 1 mA to 12 mA.

8. The method of claim 1, wherein the one or more stimulating parameters include a duty cycle comprising a 10 second ON period and a 5 second OFF period.

9. The method of claim 1, wherein the one or more stimulating parameters include a duty cycle comprising an ON period of up to 24 hours and an OFF period between 1 second to 2000 seconds.

10. The method of claim 1, wherein the one or more stimulating surfaces are each between 0.5 mm to 5 mm in length and between 0.5 mm and 1.5 mm in width.

11. The method of claim 1, wherein the one or more stimulating surfaces are each between 0.5 mm to 5 mm in length and 0.5 mm to 5 mm in width.

* * * * *